United States Patent
O'Phelan et al.

(10) Patent No.: US 6,674,634 B2
(45) Date of Patent: Jan. 6, 2004

(54) IMPLANTABLE HEART MONITORS HAVING FLAT CAPACITORS WITH CURVED PROFILES

(75) Inventors: Michael J. O'Phelan, Oakdale, MN (US); Brian L. Schmidt, Forest Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 10/287,285

(22) Filed: Nov. 4, 2002

(65) Prior Publication Data
US 2003/0058606 A1 Mar. 27, 2003

Related U.S. Application Data

(62) Division of application No. 09/705,976, filed on Nov. 3, 2000, now Pat. No. 6,522,525.

(51) Int. Cl.[7] .......................... H01G 9/045; H01G 9/10; A61N 1/40
(52) U.S. Cl. ........................... 361/509; 361/519; 607/5
(58) Field of Search ................................ 361/503, 504, 361/505–520; 607/5

(56) References Cited

U.S. PATENT DOCUMENTS

| | | | |
|---|---|---|---|
| 1,931,043 A | 10/1933 | Taylor | |
| 3,182,238 A | 5/1965 | Toder et al. | 317/260 |
| 3,643,168 A | 2/1972 | Manicki | 325/459 |
| 3,723,926 A | 3/1973 | Thomas et al. | 335/268 |
| 3,777,570 A | 12/1973 | Thomas et al. | 73/398 |
| 3,826,143 A | 7/1974 | Thomas et al. | 73/398 C |
| 3,828,227 A | 8/1974 | Millard et al. | 317/230 |
| 3,859,574 A | 1/1975 | Brazier | 317/230 |
| 3,914,666 A | 10/1975 | Schmickl et al. | 317/261 |
| 3,938,228 A | 2/1976 | Kemkers et al. | 29/25.42 |
| 3,993,508 A | 11/1976 | Erlichman | 29/623.2 |
| 4,047,790 A | 9/1977 | Carino | 339/220 |
| 4,086,148 A | 4/1978 | Badia | 204/33 |
| 4,088,108 A | 5/1978 | Hager | 123/148 CC |
| 4,131,935 A | 12/1978 | Clement | 361/433 |
| 4,169,003 A | 9/1979 | Dangel et al. | 156/179 |
| 4,232,099 A | 11/1980 | Sullivan | 429/152 |
| 4,425,412 A | 1/1984 | Dittmann et al. | 429/53 |
| 4,571,662 A | 2/1986 | Conquest et al. | 361/306 |

(List continued on next page.)

FOREIGN PATENT DOCUMENTS

| | | | |
|---|---|---|---|
| WO | WO-98/27562 | 6/1998 | H01G/4/18 |
| WO | WO-99/51302 | 10/1999 | A61N/1/375 |
| WO | WO-00/19470 | 4/2000 | |

*Primary Examiner*—Anthony Dinkins
*Assistant Examiner*—Eric Thomas
(74) *Attorney, Agent, or Firm*—Schwegman, Lundberg, Woessner & Kluth, P.A.

(57) ABSTRACT

Implantable heart-monitoring devices, such as defibrillators, pacemakers, and cardioverters, detect onset of abnormal heart rhythms and automatically apply corrective electrical therapy, specifically one or more bursts of electric charge, to abnormally beating hearts. Critical parts in these devices include the capacitors that store and deliver the bursts of electric charge. Some devices use flat aluminum electrolytic capacitors have cases with right-angle corners which leave gaps when placed against the rounded interior surfaces of typical device housings. These gaps and voids not only waste space, but ultimately force patients to endure implantable devices with larger housings than otherwise necessary. Accordingly, the inventors devised several capacitor structures that have curved profiles conforming to the rounded interior surfaces of device housings. Some exemplary capacitor embodiments include two or more staggered capacitor elements, and other embodiments stagger capacitors of different types and/or sizes.

22 Claims, 7 Drawing Sheets

U.S. PATENT DOCUMENTS

| | | | |
|---|---|---|---|
| 4,614,194 A | 9/1986 | Jones et al. | 128/419 |
| 4,616,655 A | 10/1986 | Weinberg et al. | 128/419 |
| 4,659,636 A | 4/1987 | Suzuki et al. | 429/54 |
| 4,745,039 A | 5/1988 | Yoshinaka | 429/54 |
| 4,782,340 A | 11/1988 | Czubatyj et al. | 340/825.83 |
| 4,843,518 A | 6/1989 | Okumura | 361/330 |
| 5,131,388 A | 7/1992 | Pless et al. | 128/419 D |
| 5,142,439 A | 8/1992 | Huggett et al. | 361/321 |
| 5,173,375 A | 12/1992 | Cretzmeyer et al. | 429/72 |
| 5,175,067 A | 12/1992 | Taylor et al. | 429/181 |
| 5,195,019 A | 3/1993 | Hertz | 694/328 |
| 5,279,029 A | 1/1994 | Burns | 29/856 |
| 5,306,581 A | 4/1994 | Taylor et al. | 429/181 |
| 5,367,437 A | 11/1994 | Anderson | 361/807 |
| 5,414,588 A | 5/1995 | Barbee, Jr. et al. | 361/304 |
| 5,422,200 A | 6/1995 | Hope et al. | 429/157 |
| 5,428,499 A | 6/1995 | Szerlip et al. | 361/328 |
| 5,439,760 A | 8/1995 | Howard et al. | 429/94 |
| 5,471,087 A | 11/1995 | Buerger, Jr. | 257/532 |
| 5,493,259 A | 2/1996 | Blalock et al. | 333/182 |
| 5,493,471 A | 2/1996 | Walther et al. | 361/328 |
| 5,507,966 A | 4/1996 | Liu | 252/62.2 |
| 5,522,851 A | 6/1996 | Fayram | 607/5 |
| 5,527,346 A | 6/1996 | Kroll | 607/5 |
| 5,554,178 A | 9/1996 | Dahl et al. | 607/122 |
| 5,584,890 A | 12/1996 | MacFarlane et al. | 29/25.03 |
| 5,628,801 A | 5/1997 | MacFarlane et al. | 29/25.03 |
| 5,645,586 A | 7/1997 | Meltzer | 623/11 |
| 5,658,319 A | 8/1997 | Kroll | 607/7 |
| 5,660,737 A | 8/1997 | Elias et al. | 216/6 |
| 5,691,079 A | 11/1997 | Daugaard | 429/152 |
| 5,716,729 A | 2/1998 | Sunderland et al. | 429/66 |
| 5,754,394 A | 5/1998 | Evans et al. | 361/516 |
| 5,774,261 A | 6/1998 | Omori et al. | 359/464 |
| 5,776,632 A | 7/1998 | Honegger | 429/185 |
| 5,779,699 A | 7/1998 | Lipson | 606/41 |
| 5,779,891 A | 7/1998 | Andelman | 210/198.2 |
| 5,800,724 A | 9/1998 | Habeger et al. | 216/35 |
| 5,801,917 A | 9/1998 | Elias | 361/535 |
| 5,811,206 A | 9/1998 | Sunderland et al. | 429/181 |
| 5,814,082 A | 9/1998 | Fayram et al. | 607/5 |
| 5,855,995 A | 1/1999 | Haq et al. | 428/210 |
| 5,867,363 A | 2/1999 | Tsai et al. | 361/502 |
| 5,882,362 A | 3/1999 | Muffoletto et al. | 29/623.1 |
| 5,908,151 A | 6/1999 | Elias | 228/110.1 |
| 5,922,215 A | 7/1999 | Pless et al. | 216/6 |
| 5,926,357 A | 7/1999 | Elias et al. | 361/302 |
| 5,930,109 A | 7/1999 | Fishler | 361/508 |
| 5,963,418 A | 10/1999 | Greenwood, Jr. et al. | 361/508 |
| 5,968,210 A | 10/1999 | Strange et al. | 29/25.03 |
| 5,973,906 A * | 10/1999 | Stevenson et al. | 361/302 |
| 5,983,472 A | 11/1999 | Fayram et al. | 29/25.42 |
| 6,002,969 A | 12/1999 | Machek et al. | 607/122 |
| 6,004,692 A | 12/1999 | Muffoletto et al. | 429/163 |
| 6,006,133 A | 12/1999 | Lessar et al. | 607/5 |
| 6,009,348 A | 12/1999 | Rorvick et al. | 607/5 |
| 6,032,075 A | 2/2000 | Pignato et al. | 607/5 |
| 6,040,082 A | 3/2000 | Haas et al. | 429/163 |
| 6,042,624 A | 3/2000 | Breyen et al. | 29/25.03 |
| 6,052,625 A | 4/2000 | Marshall | 607/122 |
| 6,094,788 A | 8/2000 | Farahmandi et al. | 25/24.41 |
| 6,099,600 A | 8/2000 | Yan et al. | 29/25.03 |
| 6,104,961 A | 8/2000 | Conger et al. | 607/122 |
| 6,110,233 A | 8/2000 | O'Phelan et al. | 29/25.03 |
| 6,118,651 A | 9/2000 | Mehrotra et al. | 361/509 |
| 6,139,986 A | 10/2000 | Kurokawa et al. | 429/61 |
| 6,141,205 A | 10/2000 | Nutzman et al. | 361/509 |
| 6,157,531 A | 12/2000 | Breyen et al. | 361/519 |
| 6,162,264 A | 12/2000 | Miyazaki et al. | 29/623.5 |
| 6,184,160 B1 | 2/2001 | Yan et al. | 438/800 |
| 6,191,931 B1 | 2/2001 | Paspa et al. | 361/302 |
| 6,212,063 B1 | 4/2001 | Johnson et al. | 361/517 |
| 6,225,778 B1 | 5/2001 | Hayama et al. | 320/112 |
| 6,249,423 B1 | 6/2001 | O'Phelan et al. | 361/502 |
| 6,249,709 B1 | 6/2001 | Conger et al. | 607/122 |
| 6,256,542 B1 | 7/2001 | Marshall et al. | 607/126 |
| 6,259,954 B1 | 7/2001 | Conger et al. | 607/122 |
| 6,275,729 B1 | 8/2001 | O'Phelan et al. | 607/5 |
| 6,297,943 B1 | 10/2001 | Carson | 361/500 |
| 6,299,752 B1 | 10/2001 | Strange et al. | 205/152 |
| 6,321,114 B1 | 11/2001 | Nutzman et al. | 607/5 |
| 6,326,587 B1 | 12/2001 | Cardineau et al. | 219/121.68 |
| 6,388,866 B1 | 5/2002 | Rorvick et al. | 361/503 |
| 6,402,793 B1 | 6/2002 | Miltich et al. | 29/25.03 |
| 6,442,015 B1 | 8/2002 | Niiori et al. | 361/502 |
| 6,477,037 B1 | 11/2002 | Nielsen et al. | 361/520 |
| 6,493,212 B1 | 12/2002 | Clarke et al. | 361/521 |
| 6,522,525 B1 | 2/2003 | O'Phelan et al. | 361/509 |

* cited by examiner

IMPLANTABLE HEART MONITORS HAVING FLAT CAPACITORS WITH CURVED PROFILES

CROSS-REFERENCE TO RELATED APPLICATIONS

This application is a division of U.S. application Ser. No. 09/705,976, filed on Nov. 3, 2000, now issued as U.S. Pat. No. 6,522,525, the specification of which is incorporated by reference herein.

This application is related to U.S. application Ser. No. 09/706,447, filed on Nov. 3, 2000, entitled FLAT CAPACITOR FOR AN IMPLANTABLE MEDICAL DEVICE, which is incorporated herein by reference in its entirety.

TECHNICAL FIELD

This invention relates generally to electrolytic capacitors and, more particularly to flat electrolytic capacitors for use in implantable heart monitors.

BACKGROUND OF THE INVENTION

Since the early 1980s, thousands of patients prone to irregular and sometimes life threatening heart rhythms have had miniature heart-monitoring devices, such as defibrillators, pacemakers, and cardioverters, implanted in their bodies. These devices detect onset of abnormal heart rhythms and automatically apply corrective electrical therapy, specifically one or more bursts of electric current, to their hearts. When the bursts of electric current are properly sized and timed, they restore normal heart function without human intervention, sparing patients considerable discomfort and often saving their lives.

The typical implantable heart-monitoring device includes a set of electrical leads, which extend from a sealed housing for implantation into the inner walls of a heart. The housing itself is typically somewhat flat and rectangular with rounded edges and corners to reduce stress on surrounding tissues after implantation. Within the housing are a battery for supplying power, heart-monitoring circuitry for monitoring the heart and detecting abnormal rhythmic conditions, and two or more capacitors for delivering bursts of electric current through the leads to the heart.

In many instances, each capacitor takes the form of a flat aluminum electrolytic capacitor. This type of capacitor generally includes a vertical stack of several flat D-shaped capacitor elements, or modules, with each module comprising at least one D-shaped paper separator sandwiched between D-shaped sheets of aluminum foil. The capacitor modules are electrically coupled together to provide a total capacitance and then housed in a D-shaped case made of aluminum or another metal compatible with the foil.

The aluminum case, which conforms closely to the shape of the vertical stack of D-shaped capacitor modules, has vertical sidewalls that are parallel to the vertical faces of the stack. The case also has D-shaped top and bottom portions that meet its vertical sidewalls to form approximate right-angle joints and corners along its top and bottom edges.

Two or more such capacitors are sometimes stacked on top of each other within the housing of an implantable device. When stacked, the walls of the D-shaped capacitors are aligned with each other, effectively forming a single vertical wall the combined height of the capacitors.

One problem with these types of flat capacitors and their stacked arrangement in implantable device housings is that the walls of the cases are incompatible with the rounded edges and corners of implantable device housings. Juxtaposing these vertical walls and right-angle corners against the rounded interior portions of the housings inevitably leaves gaps or voids between the cases and housings. These voids not only waste space, but ultimately force patients to endure implantable devices with larger housings than otherwise necessary.

Accordingly, there is a need for flat capacitors that better conform to the rounded portions of implantable medical-device housings.

SUMMARY

To address this and other needs, the inventors devised new capacitor structures, new capacitor shapes, and new capacitor assemblies to conform better with the housings of implantable medical devices. One exemplary capacitor includes three or more capacitive modules that are sized and stacked so that their edges on at least one side are staggered relative each other in one or two dimensions to define a curved profile that conforms generally with a rounded, interior surface of a capacitor case.

The inventors also devised new capacitor shapes, some of which incorporate one or more rounded corners. One exemplary capacitor includes a main portion and two peninsular portions extending from one side of the main portion, defining a "U." Terminals extend from the end of one of the peninsular portions. One innovative use of this shape entails placing a battery or other component of an implantable medical device in the region between the two peninsular portions.

Additionally, the inventors devised new capacitor assemblies. One exemplary capacitor assembly includes two or more separate capacitors of different sizes. In some embodiments, one or more of these capacitors include a curved profile and/or are staggered relative each other. In other embodiments, two or more capacitors of the same size are staggered relative each other.

Other aspects of the invention include an implantable medical device, such as a pacemaker, defibrillator, cardioverter-defibrillator, or congestive-heart-failure device, that has a housing with at least one rounded surface abutting the rounded portion of a capacitor. The capacitor includes a capacitive stack with a curved profile and/or includes a pair of peninsular portions spaced to receive a battery or other component. Other implantable devices include one or more of the new capacitive assemblies.

DETAILED DESCRIPTION OF THE EMBODIMENTS

The following detailed description, which references and incorporates the above-identified figures, describes and illustrates one or more specific embodiments of the invention. These embodiments, offered not to limit but only to exemplify and teach, are shown and described in sufficient detail to enable those skilled in the art to implement or practice the invention. Thus, where appropriate to avoid obscuring the invention, the description may omit certain information known to those of skill in the art.

As used herein, the term "profile" refers to the general outline of a portion of an object taken in or projected onto a plane generally perpendicular to a major surface of the object. Thus, for example, in some flat capacitors, profile means the outline of the capacitor case and/or the capacitor stack taken in a plane perpendicular to the major surfaces of the case or the capacitor stack.

As used herein, the term "staggered" refers to the existence of an offset between respective adjacent surfaces of two or more juxtaposed or proximate objects. Thus, for example, the offset can result from offsetting one of the objects relative the other object or controlling the relative size and placement of the objects.

Figure 1:
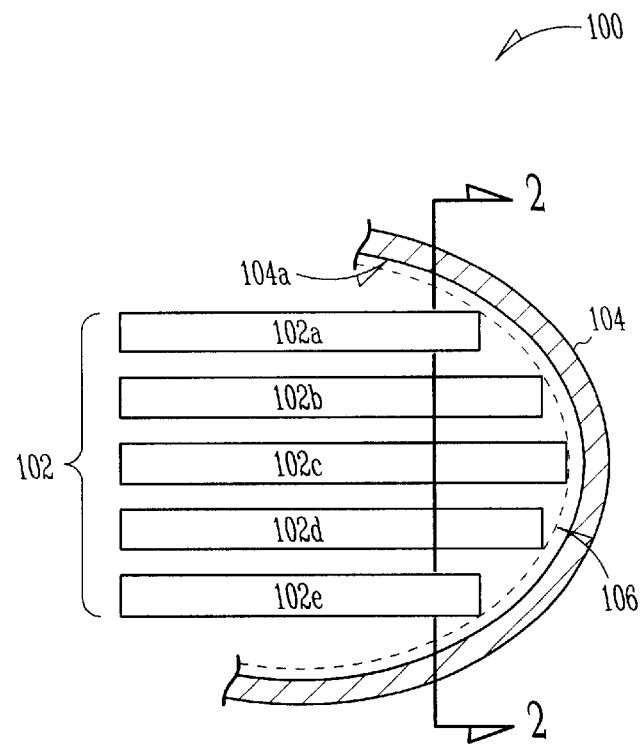
FIG. 1 is a partial cross-sectional view of an exemplary capacitor 100 having capacitor modules with edges staggered in a first dimension to define a curved profile 106.

FIG. 1 shows a portion of an exemplary capacitor 100 incorporating the present invention. Capacitor 100 includes a stack 102 of two or more electrically coupled capacitor modules 102a, 102b, 102c, 102d, and 102e within a capacitor case 104. Modules 102a–102e are staggered so that their edges generally (or at least a portion of side of the stack) define a profile 106 that generally conforms or is substantially congruent to an adjacent curved interior portion 104a of capacitor case 104.

Figure 2:
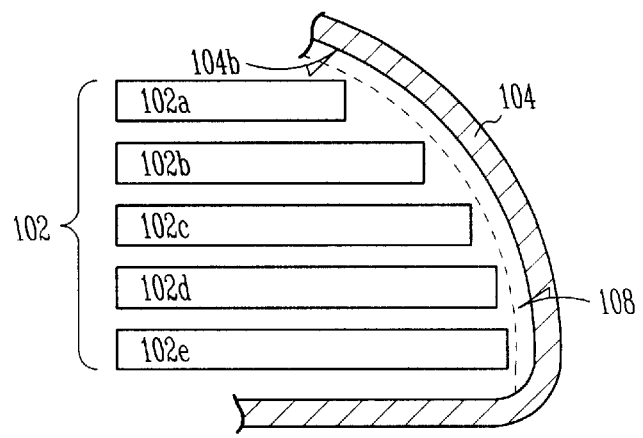
FIG. 2 is a partial cross-sectional view of capacitor 100 showing that its capacitor modules are staggered in a second dimension to define another curved profile 108.

FIG. 2, a section view of capacitor 100 taken along line 2—2, shows that modules 102a–102e are staggered in two dimensions. In this view, capacitor modules 102a–102e define a profile 108, which is generally congruent to a curved portion 104b of case 104. Although profiles 106 and 108 are quite distinct in this exemplary embodiment, other embodiments make profiles 106 and 108 substantially congruent.

In the exemplary embodiment, each capacitor module includes a three-layer etched and/or perforated anode, a cathode, and at least one electrolyte-carrying separator between the anode and the cathode. The anode and cathode comprise foils of aluminum, tantalum, hafnium, niobium, titanium, zirconium, or combinations of these metals. Additionally, each capacitor module is sandwiched between two pairs of electrolyte-carrying separators, with the separators extending beyond the anode and cathode to prevent undesirable shorting with the case. Alternatively, separate insulative layer can be placed between the capacitor modules and the case interior walls to prevent shorting. Exemplary separators comprise kraft paper, and exemplary electrolytes include ethylene-glycol base combined with butrylactone.

In other embodiments, the capacitor modules take other forms having different numbers of anode layers and separators. For example, in some embodiments, the anodes, cathode, and separators in one or more of the capacitor modules are staggered to define curved module faces that confront the interior surfaces 104a or 104b of the case. Also, in some embodiments, one or more of the anodes or cathodes are coupled to the case, making it either anodic or cathodic.

To define the staggered edge faces and thus the curved profile, some embodiments which provide the curved profile in a single dimension, use a set of generally congruent modules of different sizes. For example, one embodiment includes four generally D-shaped modules, each with a common width and height, but with four successively smaller lengths. The modules are stacked, each module having at least one edge aligned vertically with the corresponding edges of adjacent modules.

Figure 3:
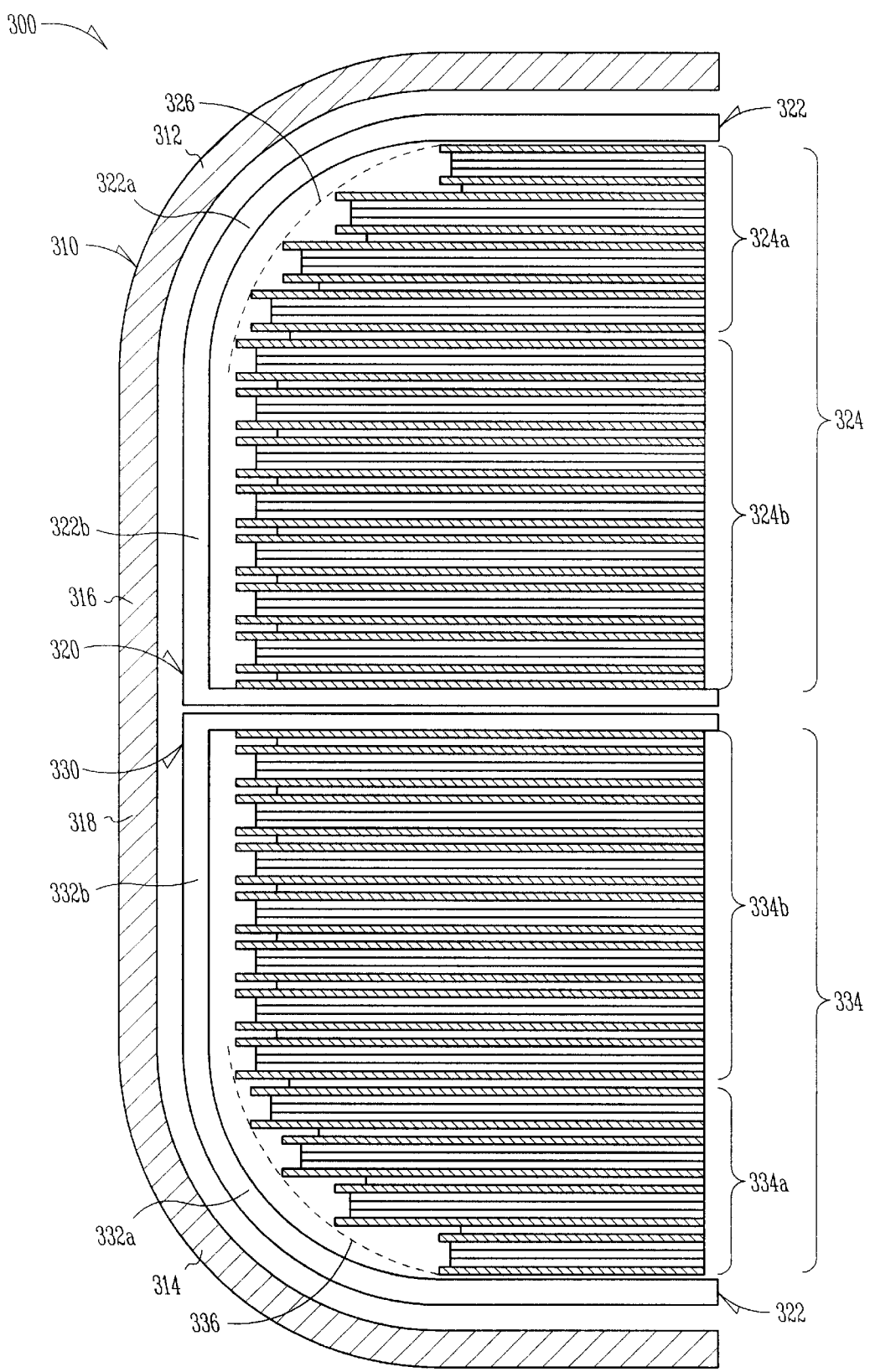
FIG. 3 is a partial cross-sectional view of an exemplary implantable heart monitor 300 including a monitor housing 310 and two capacitors 320 and 330 having curved profiles that abut interior curved portions of the monitor housing.

FIG. 3 shows an exemplary implantable heart monitor 300 including a monitor housing 310 and two capacitors 320 and 330. Monitor housing 310 includes curved portions 312 and 314 and adjoining straight portions 316 and 318. Capacitor 320 includes case 322 and eleven capacitor modules 324. Case 322 includes a curved portion 322a and a straight portion 322b, respectively confronting curved portion 312 and straight portion 316 of housing 310.

Capacitor modules 324 include a set of staggered modules 324a and a set of unstaggered modules 324b. The set of staggered modules 324a confront curved portion 322a of case 322 and have edges arranged to define a curved profile 326 generally congruent to the profile of curved portion 322. Modules 324b, which are vertically aligned, confront straight portion 322b of case 322.

Similarly, capacitor 330 includes case 332 and eleven capacitor modules 334. Case 332 includes curved portion 332a and a straight portion 332b, which confront respective portion 314 and 318 of housing 310. Capacitor modules 334 include staggered modules 334a, which confront curved portion 332a of case 332, have front edges arranged to define a curved profile 336 generally congruent to the profile of curved portion 332a. Modules 334b confront straight portion 332b of case 332.

Notably, the exemplary embodiment provides each of modules 324 and 334 with three anodes placed between one or more separators and at least one cathode placed adjacent one of the separators. (FIG. 3 shows the separators crosshatched.) However, the invention is not limited to any particular module arrangement. Indeed, some embodiments of the invention use other (greater or lesser) numbers of anodes as well as modules. Moreover, some embodiments mix modules of different arrangements within the same capacitor case. This allows greater flexibility in exploiting the space available in the case as well as the housing. For more details, see co-assigned and co-pending U.S. patent application which is entitled Mixing of Multiple Anodes within a single aluminum Electrolytic Flat Capacitor (attorney docket 279.264US1) which is incorporated herein by reference.

Additionally, other embodiments of the invention construct capacitor cases 322 and 332 as a single case having two adjacent compartments with a common wall. Modules 324 and 334 are each placed in a respective compartment. The cathodes in modules 324 and the anodes of modules 334 are electrically coupled to the case; an external anode terminal is coupled to the anodes of module 324; and an external cathode terminal is coupled to the cathodes of module 334, thereby effecting a series connection of the two capacitors using two external terminals instead of the four that are conventionally provided.

This arrangement can be made by providing two (first and second) aluminum case bodies having the desired curved portions, placing capacitor modules in the first case body, and welding a cover to the first case body. Other capacitor modules can then be stacked and placed in the second case body. The cover of the first case body is then put on the opening of the second case body and welded in place. For further details, see co-pending and co-assigned U.S. patent application which is entitled Multi-Compartment Electrolytic Capacitor (attorney docket 279.264US1), and which is incorporated herein by reference.

Figure 4:
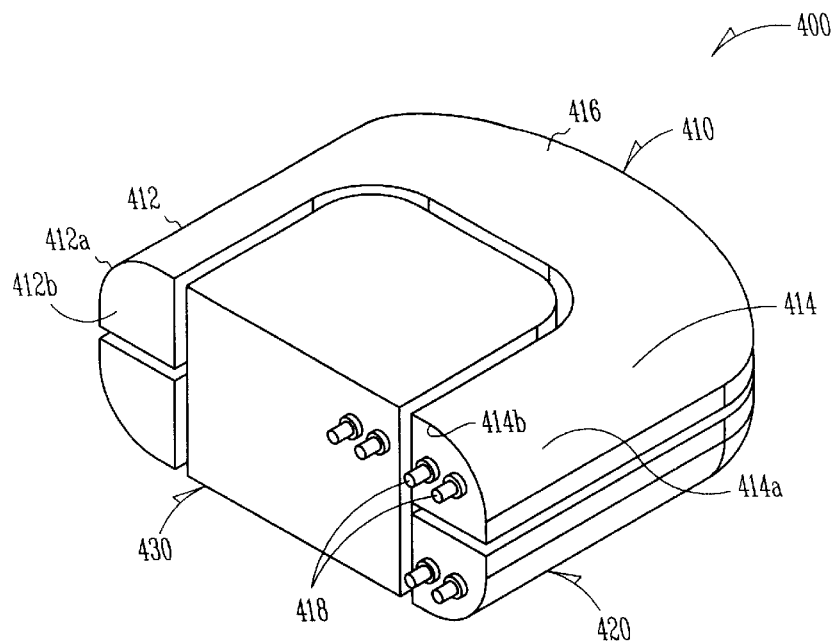
FIG. 4 is a perspective view of an exemplary capacitor-battery assembly 400 including two stacked U-shaped capacitors 410 and 420 and a battery 430 nested within the capacitors.

FIG. 4 shows a perspective view of an exemplary capacitor-battery assembly 400 including two stacked U-shaped capacitors 410 and 420 and a battery 430 nested within the capacitors. For sake of brevity, capacitor 420, which is of substantially identical size, shape, and structure as capacitor 410 in this exemplary assembly, is not described separately. However, the invention is not so limited. Capacitor 410 includes legs 412 and 414, respective middle (or intermediate) portions 416, and terminals 418. Legs 412 and 414, which are parallel in the exemplary embodiment, include respective curved surfaces 412*a* and 414*a*, and respective flat end surfaces 412*b* and 414*b*.

Figure 5:
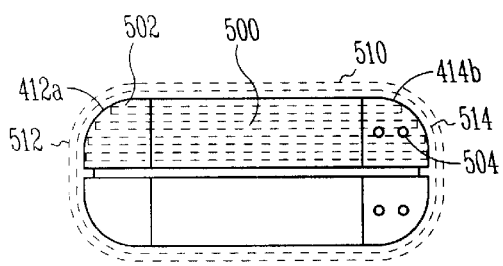
FIG. 5 is a front view of the FIG. 4 assembly without the battery.

FIG. 5, a front view of assembly 400 without battery 430, shows that curved surfaces 412*a* and 414*b* are generally congruent to each other and to respective curved profile 502 and 504 defined by capacitor modules 500. Further, it shows a housing 510 (in phantom) having a curved or concave portions 512 and 514 generally congruent with or conformant to curved (or convex) surfaces 412*a* and 414*a*. In the exemplary embodiment, curved profiles 502 and 504 are quarter segments of an ellipse or circle, and surfaces 412*a* and 414*a* are portions of an ellipsoid or sphere. The exemplary embodiment provides the modules with one or more of the single or multiple anode structures noted previously. Thus, modules 500 may include modules with differing anode structures as desired to fit a given height.

Figure 6:
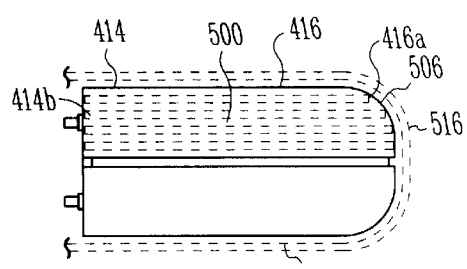
FIG. 6 is a side view of the FIG. 4 assembly.

FIG. 6, a side view of assembly 400, shows that the curved surfaces 412*a* and 414*a* are generally perpendicular to end surfaces 412*a* and 412*b*. Middle portion 416 is also shown as having a curved portion 416*a* which is congruent to a curved profile 506 defined by capacitor modules 500 and a curved portion 516 of monitor housing 510.

Figure 7:
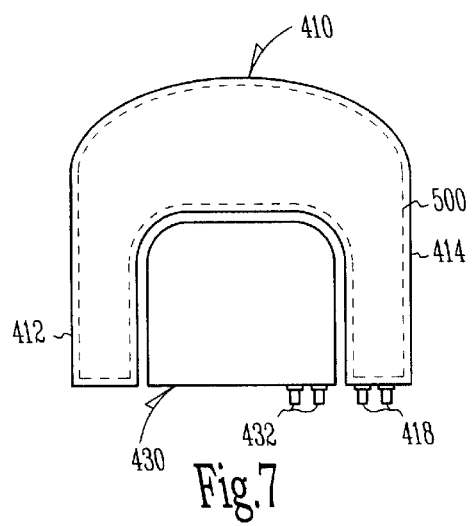
FIG. 7 is a top view of the FIG. 4 assembly.

FIG. 7 is a top view of assembly 400, showing the general U-shape of capacitor modules 500. This figure also shows that battery 430 includes terminals 432.

Figure 8:
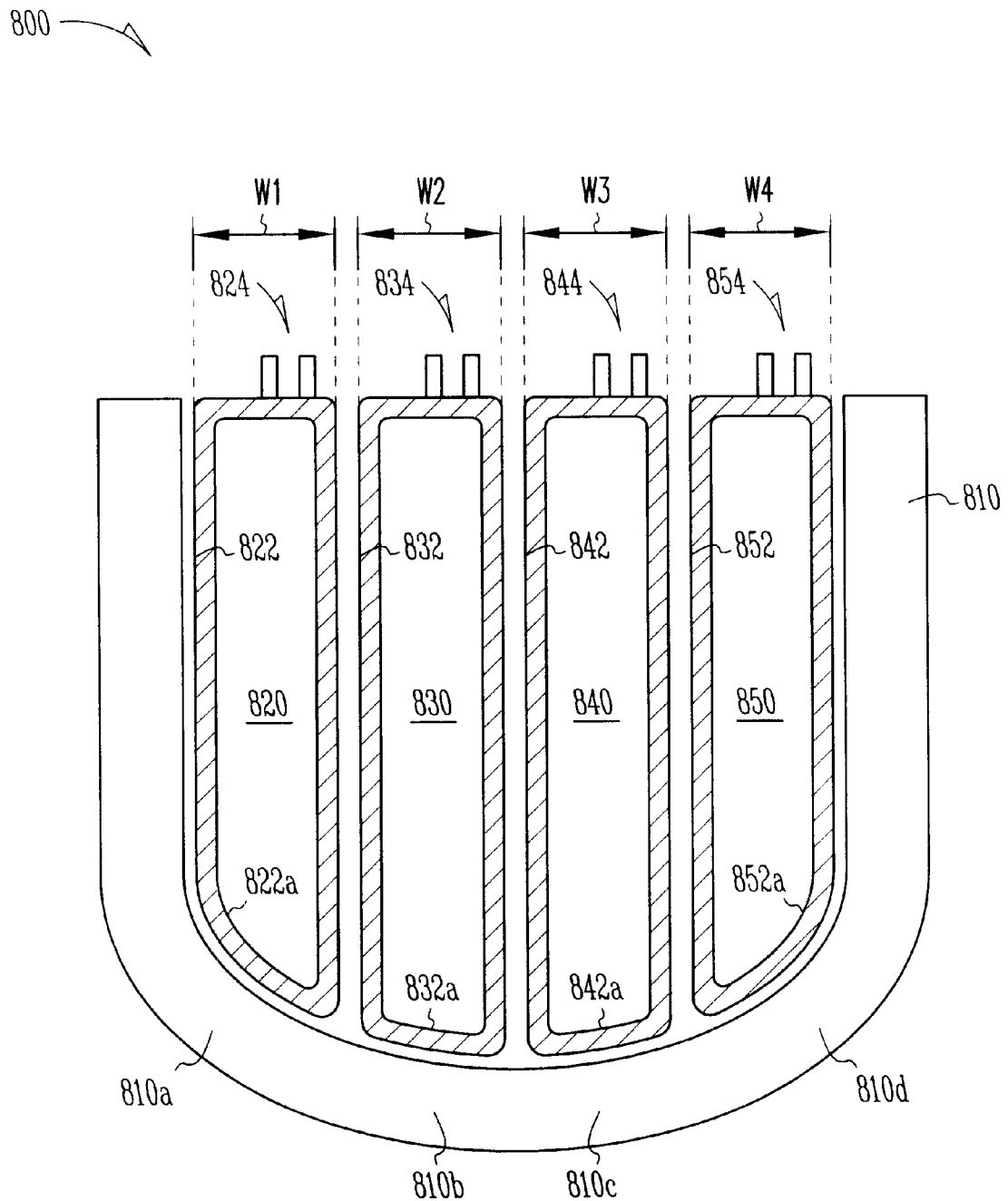
FIG. 8 is a partial cross-sectional view of an exemplary capacitor assembly 800.
Figure 9:
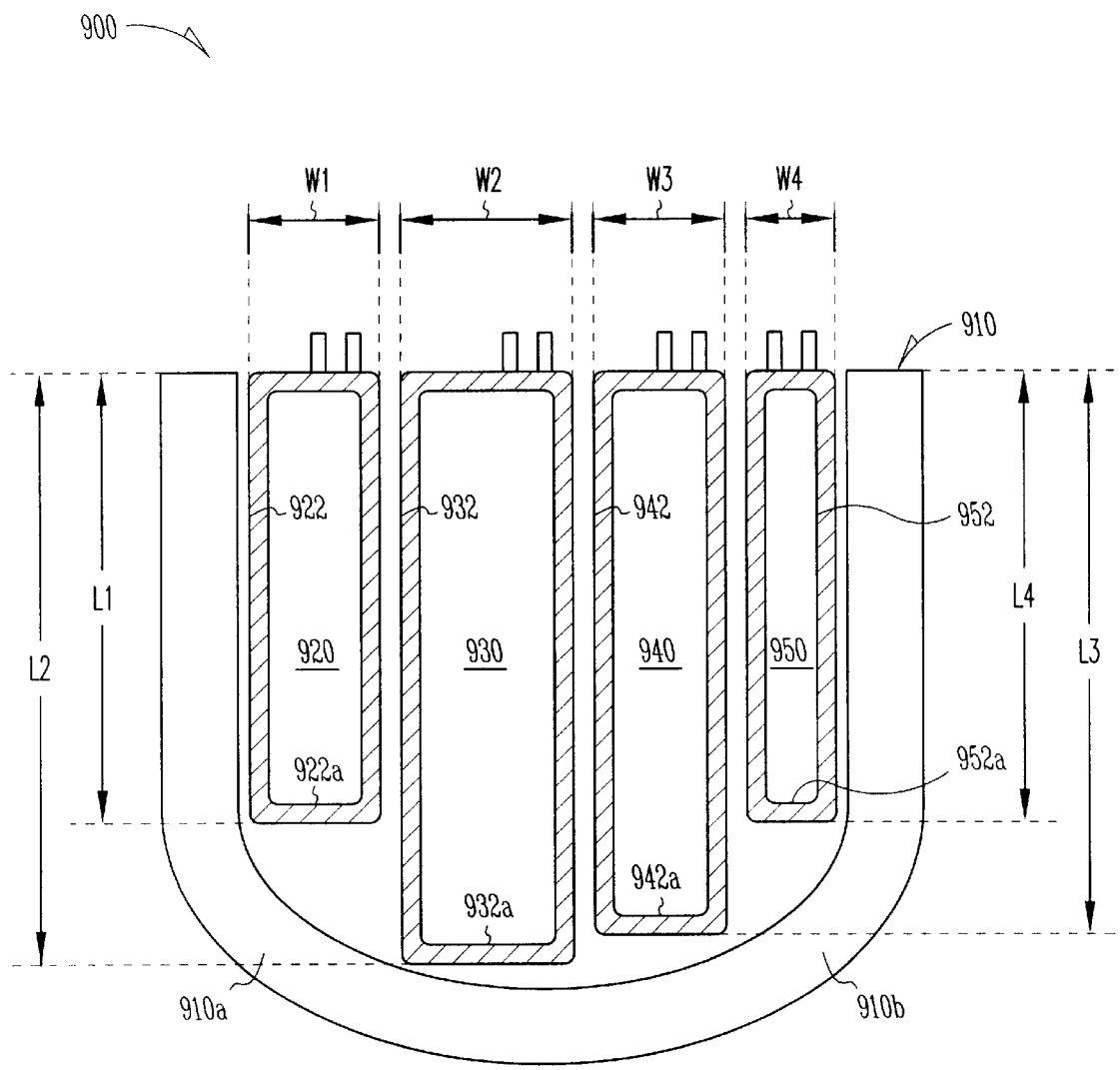
FIG. 9 is a partial cross-sectional view of an exemplary capacitor assembly 900.
Figure 10:
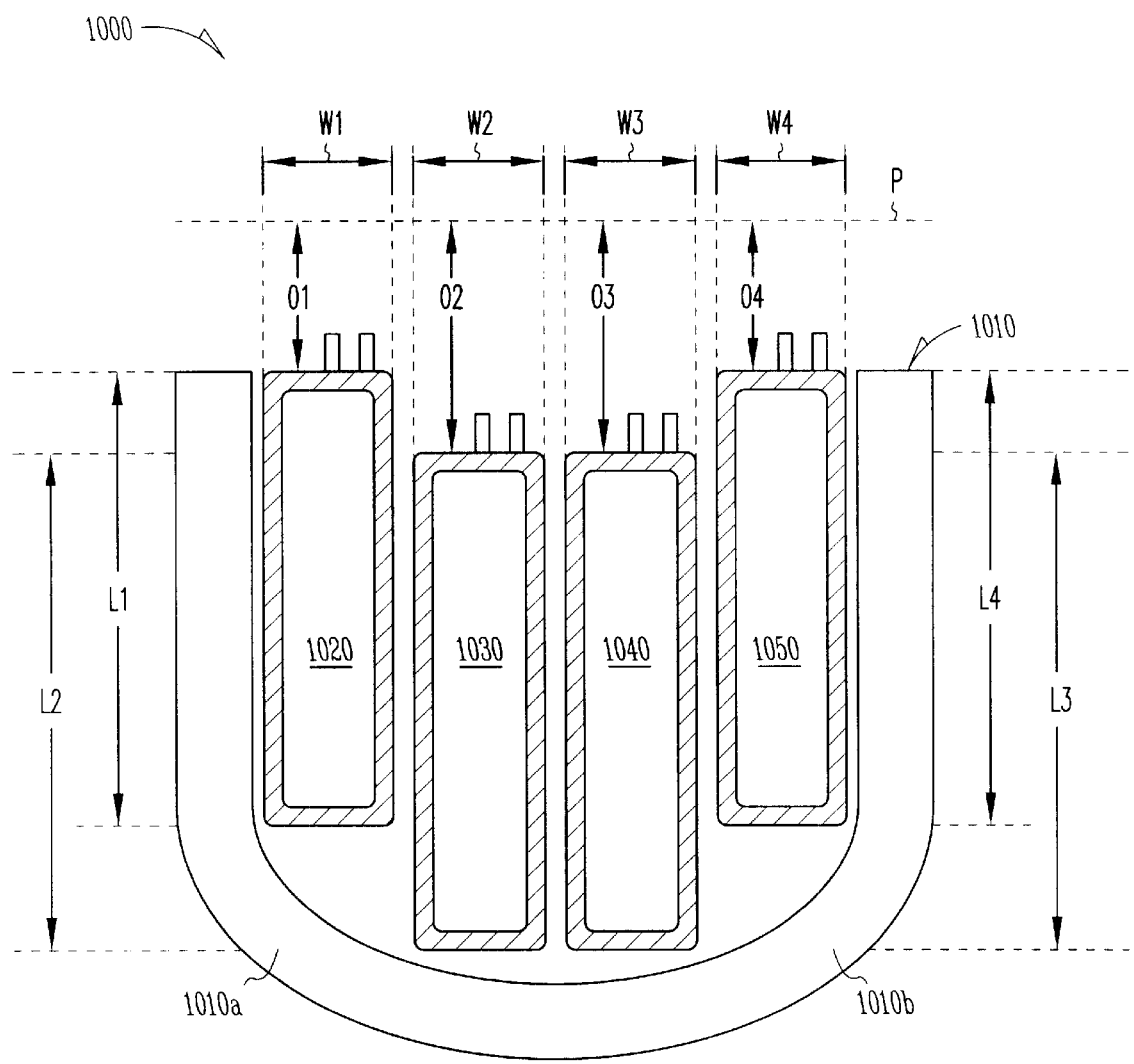
FIG. 10 is a partial cross-sectional view of an exemplary capacitor assembly 1000.

FIGS. 8, 9, and 10, all cross-sectional views, show respective four-capacitor assemblies, each illustrating a flexible capacitor-level approach to reducing the voids in implantable-device housings. In a mass-production context, the capacitor-level approach allows one to prefabricate a set of capacitors of different sizes, different curvatures, and even of different capacitor technologies, and then to assemble the capacitors to conform to the available space within a housing.

In particular, FIG. 8, a cross-sectional view, shows an exemplary capacitor assembly 800. Capacitor assembly 800 includes a monitor housing 810 and four separate capacitors 820, 830, 840, and 850. Housing 810 includes curved portions 810*a*, 810*b*, 810*c*, and 810*d*. Capacitors 820, 830, 840, and 850 include respective capacitor cases 822, 832, 842, and 852, and respective terminals pairs 824, 834, 844, and 854. (For clarity, the figure omits the internals of these capacitors.) Cases 822, 832, 842, and 852 have respective curved portions 822*a*, 832*a*, 842*a*, and 852*a* that are generally congruent to and confront respective curved portions 810*a*, 810*b*, 810*c*, and 810*d* of housing 810. The cases also have respective widths (or heights) W1, W2, W3, and W4 Each of capacitors terminal pairs 824, 834, 844, and 854 includes an anode terminal and a cathode terminal. Though not shown, the exemplary embodiment interconnects the terminals to achieve a series connection of two capacitances.

This exemplary embodiment provides the four capacitors with a common width. However, other embodiments provide one or more of the capacitors with a different width. For example, in some embodiments, widths W1 and W4 are equal, and widths W2 and W3 are equal, but different from widths W1 and W2. Additionally, two or more of the capacitors, for example, capacitors 820 and 830 or capacitors 820 and 830, can be combined into a single capacitor. And, still other embodiments use different numbers of capacitors, such as three, five, or six. Thus, the invention is not limited to an particular number of capacitors.

FIG. 9, a cross-sectional view, shows an exemplary capacitor assembly 900. Capacitor assembly 900 includes a monitor housing 910 and four separate capacitors 920, 930, 940, and 950. Housing 910 includes curved portions 910*a* and 910*b*. Capacitors 920, 930, 940, and 950 include respective capacitor cases 922, 932, 942, and 952, which have respective widths (or heights) W1, W2, W3, and W4, and respective lengths L1, L2, L3, and L4. Cases 922 and 932 have respective end walls 922*a* and 932*a* which confront curved portion 910*a*; and cases 942 and 952 have respective end walls that confront curved portion 910*b*.

In this exemplary embodiment, the capacitors lack individual curved profiles, but have different sizes to reduce voids between their respective cases and the monitor housing. More precisely, one or more of the capacitors has a different width and/or length. As shown, lengths L1 and L4 are equal to a length LA, and lengths L2 and L3 are equal to a different length LB. Also, widths W2 and W3 are equal to a width WA, and widths W1 and W4 are not equal to each other or to the width WA. However, in some embodiments, the capacitors have a common width.

FIG. 10, a cross-sectional view, shows an exemplary capacitor assembly 1000. Capacitor assembly 1000 includes a monitor housing 1010 and four separate capacitors 1020, 1030, 1040, and 1050. Housing 1010 includes curved portions 1010*a* and 1010*b*. Capacitors 1020, 1030, 1040, and 1050 include respective capacitor cases 1022, 1032, 1042, and 1052. Cases 1022, 1032, 1042, and 1052 have respective widths W1, W2, W3, and W4, and respective lengths L1, L2, L3, and L4. Additionally, cases 1022, 1032, 1042, and 1052 are offset from a common reference plane P by respective offsets O1, O2, O3, and O4.

In this exemplary embodiment, widths W1, W2, W3, and W4 are equal, and lengths L1, L2, L3, and L4 are equal. Further, offsets 01 and 04 are equal, and offsets O2 and O3 are equal but larger than offsets O1 and O4. In other embodiments, each of the offsets is larger than the previous offset, creating descending steps.

In the exemplary embodiments of FIGS. 8–10, the four capacitors are aluminum electrolytic capacitors, with each capacitor including one or more capacitor modules of similar or dissimilar structures (as previously described for other exemplary capacitors.) However, other embodiments provide the four capacitors as wet-tantalum, ceramic, dry-film capacitors, or other types of capacitors. Still other embodiments provide combinations of different numbers of capacitors and different types of capacitors.

Figure 11:
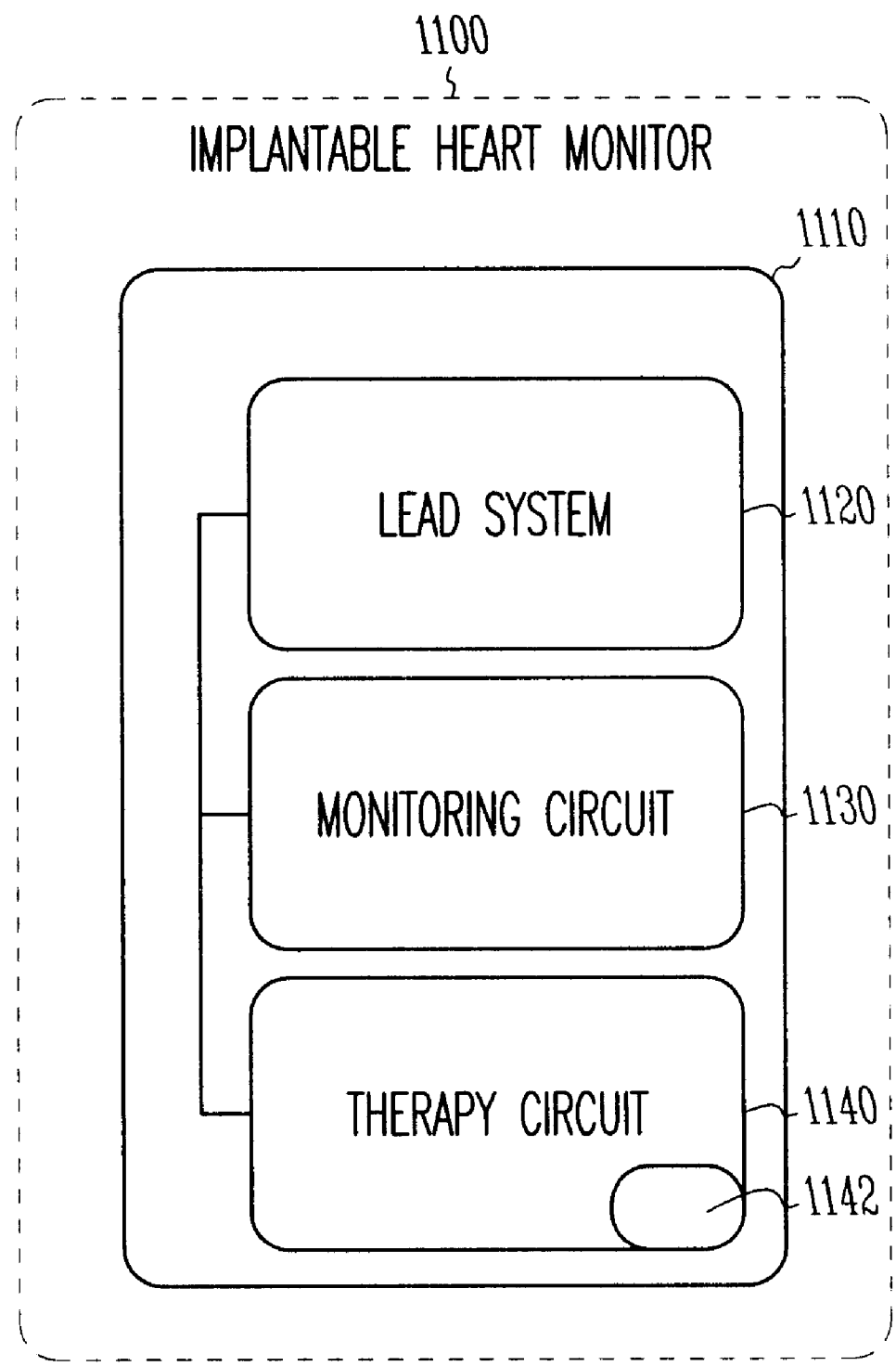
FIG. 11 is a block diagram of an implantable heart monitor 1100.

FIG. 11 is a block diagram of implantable heart monitor 1100 which incorporates one or more teachings of the present invention. Specifically, monitor 1100 includes a housing 1110, lead system 1120, which after implantation electrically contact strategic portions of a patient's heart, a monitoring circuit 1130 for monitoring heart activity through one or more of the leads of lead system 1120, and a therapy circuit 1140. Circuit 1140 includes a component 1142 which incorporates one or more capacitors, such as capacitors 100 and 300, capacitor-battery assembly 400, or one or more of capacitor assemblies 800, 900, or 1000. Monitor 1100 operates according to well known and understood principles to perform defibrillation, cardioversion, pacing, and/or other therapeutic functions.

In addition to its application to implantable heart monitors, or cardiac rhythm management devices, the teachings of the present invention are applicable to photographic flash equipment. Indeed, these teachings are pertinent to any application where small, high-energy capacitors are desirable.

CONCLUSION

In furtherance of the art, the present inventors have devised several new capacitor structures having curved profiles and capacitor assemblies for reducing voids in implantable medical devices. The curved profiles generally facilitate efficient use of curved capacitor cases and curved housings for implantable medical devices. In some exemplary embodiments, the capacitors include staggered capacitor modules or elements to define the curved profiles, and in other embodiments, the capacitors themselves are staggered.

The embodiments described above are intended only to illustrate and teach one or more ways of practicing or implementing the present invention, not to restrict its breadth or scope. The actual scope of the invention, which embraces all ways of practicing or implementing the teachings of the invention, is defined only by the following claims and their equivalents.

What is claimed is:

1. A multiple-capacitor assembly for an implantable heart monitor, the assembly comprising:
   a first capacitor having a first case wall, a first pair of terminals, and a first nominal size; and
   a second capacitor having a second case wall, a second pair of terminals, and a second nominal size with the second case wall being conductive and confronting the first case wall, at least one of the second pair of terminals coupled to at least one of the first pair of terminals, and with the second nominal size being different than the first nominal size.

2. The multiple-capacitor assembly of claim 1, wherein the first capacitor has a first nominal length and the second capacitor has a second nominal length that differs from the first nominal length.

3. The multiple-capacitor assembly of claim 1, wherein the first capacitor is one of the group consisting of an aluminum electrolytic capacitor, a wet-tantalum capacitor, a dry-film capacitor, and a ceramic capacitor and wherein the second capacitor is a different one of the group.

4. The multiple-capacitor assembly of claim 1, wherein the first capacitor has a first nominal width and the second capacitor has a first nominal width that is different from the first nominal width.

5. An implantable medical device comprising a multiple-capacitor assembly, wherein the assembly includes:
   a first capacitor having a first case wall, a first pair of terminals, and a first nominal size; and
   a second capacitor having a second case wall, a second pair of terminals, and a second nominal size, with the second case wall being conductive and confronting the first case wall, at least one of the second pair of terminals coupled to at least one of the first pair of terminals, and with the second nominal size being different than the first nominal size.

6. The implantable medical device of claim 5, further comprising a medical-device housing containing the first and second capacitors and having a curved interior surface, wherein the second case wall includes a curved portion confronting the curved interior surface.

7. A multiple-capacitor assembly for an implantable heart monitor,
   the assembly comprising:
   a first capacitor having a first pair of terminals, a first conductive case wall, and a first nominal size; and
   a second capacitor having a second pair of terminals, a second conductive case wall, and a second nominal size, with at least one of the second pair of terminals coupled to at least one of the first pair of terminals, with the second case wall offset from the first case wall, and with the second nominal size the same as the first nominal size.

8. The multiple-capacitor assembly of claim 7, further comprising:
   a third capacitor positioned adjacent the first capacitor and having a third pair of terminals, a third case wall, and a third nominal size, with at least one of the third pair of terminals coupled to at least one of the first or second pair of terminals, with the third case wall substantially flush with the first or second conductive case wall.

9. The multiple-capacitor assembly of claim 8, wherein the third nominal size differs from the first nominal size.

10. The multiple-capacitor assembly of claim 7, wherein the first capacitor is an aluminum electrolytic capacitor, and wherein the second capacitor is not an aluminum electrolytic capacitor.

11. An implantable medical device comprising a multiple-capacitor assembly, wherein the assembly includes:
    a first capacitor having a first pair of terminals, a first conductive case wall, and a first nominal size; and
    a second capacitor having a second pair of terminals, a second conductive case wall, and a second nominal size, with at least one of the second pair of terminals coupled to at least one of the first pair of terminals, with the second conductive case wall offset from the first case wall, and with the second nominal size the same as the first nominal size.

12. The implantable medical device of claim 11, further comprising a medical-device housing containing the first and second capacitors and having a curved interior surface, wherein the second conductive case wall includes a curved portion confronting the curved interior surface.

13. An implantable medical device comprising a multiple-capacitor assembly, wherein the assembly includes:
    a first capacitor having a first pair of terminals, a first conductive case wall, and a first nominal size;
    a second capacitor having a second pair of terminals, a second conductive case wall, and a second nominal size, with at least one of the second pair of terminals coupled to at least one of the first pair of terminals, with the second conductive case wall offset from the first case wall, and with the second nominal size the same as the first nominal size; and
    a third capacitor positioned adjacent the first capacitor and having a third pair of terminals, a third case wall, and a third nominal size, with at least one of the third pair of terminals coupled to at least one of the first or second pair of terminals, with the third case wall substantially flush with the first or second conductive case wall.

14. The implantable medical device of claim 13, further comprising a medical-device housing containing the first and second capacitors and having a curved interior surface, wherein the second case wall includes a curved portion confronting the curved interior surface.

15. An implantable medical device comprising a multiple-capacitor assembly, wherein the assembly includes:

a first capacitor having a first pair of terminals, a first conductive case wall, and a first nominal size;

a second capacitor having a second pair of terminals, a second conductive case wall, and a second nominal size, with at least one of the second pair of terminals coupled to at least one of the first pair of terminals, with the second conductive case wall offset from the first case wall, and with the second nominal size the same as the first nominal size; and a third capacitor positioned adjacent the first capacitor and having a third pair of terminals, a third case wall, and a third nominal size, with at least one of the third pair of terminals coupled to at least one of the first or second pair of terminals, with the third case wall substantially flush with the first or second conductive case wall, and the third nominal size differs from the first nominal size.

16. The implantable medical device of claim 15, further comprising a medical-device housing containing the first and second capacitors and having a curved interior surface, wherein the second conductive case wall includes a curved portion confronting the curved interior surface.

17. A multiple-capacitor assembly for an implantable heart monitor, the assembly comprising:

a first capacitor having a first conductive case, a first pair of terminals, and a first nominal size, with the first conductive case at least partially enclosing at least first and second capacitor modules and at least one electrolyte-carrying separator between the modules; and a second capacitor having a second conductive case, a second pair of terminals, a second nominal size, with the second conductive case having a wall confronting the first conductive case, at least one of the second pair of terminals coupled to at least one of the first pair of terminals, and with the second nominal size being different than the first nominal size.

18. The multiple-capacitor assembly of claim 17, wherein the first capacitor has a first nominal length and the second capacitor has a second nominal length that differs from the first nominal length.

19. The multiple-capacitor assembly of claim 17, wherein the first capacitor is an aluminum electrolytic capacitor.

20. The multiple-capacitor assembly of claim 17, wherein the second conductive case at least partially encloses third and fourth capacitive modules and at least one electrolyte-carrying separator between the third and fourth modules.

21. The multi-capacitor assembly of claim 17, wherein each capacitor module comprises at least one cathode, at least one multi-layered anode, and at least one electrolyte-carrying separator between the one cathode and the one multi-layered anode.

22. The multi-capacitor assembly of claim 17, wherein the electrolyte-carrying separator carries an electrolyte having an ethylene-glycol base.

* * * * *